United States Patent [19]

Kropf et al.

[11] Patent Number: 5,522,825
[45] Date of Patent: Jun. 4, 1996

[54] MEDICAL INSTRUMENT FOR THE REMOVAL OF DEPOSITS FORMED ON THE INNER WALLS OF THE ARTERIES OR VEINS

[75] Inventors: Laurent Kropf, Penthaz; Hugues Baumgartner, Mollie-Margot; Umberto Damone, Lausanne, all of Switzerland

[73] Assignee: Ferromec S.A., Vufflens-la-Ville, Switzerland

[21] Appl. No.: 217,364

[22] Filed: Mar. 24, 1994

[30] Foreign Application Priority Data

Mar. 25, 1993 [CH] Switzerland ............... 914/93

[51] Int. Cl.$^6$ ............... A61B 10/00; A61B 17/22
[52] U.S. Cl. ............... 606/159; 606/170; 604/22; 128/751
[58] Field of Search ............... 606/159, 170; 128/751, 757; 604/22

[56] References Cited

U.S. PATENT DOCUMENTS

| 4,747,821 | 5/1988 | Kensey | 604/22 |
|---|---|---|---|
| 4,765,332 | 8/1988 | Fischell et al. | 606/159 X |
| 4,794,928 | 1/1989 | Kletschka | 606/159 |
| 4,886,061 | 12/1989 | Fischell et al. | 606/159 |
| 4,957,482 | 9/1990 | Shiber | 604/22 |
| 4,966,604 | 10/1990 | Reiss | 606/170 X |
| 5,030,201 | 7/1991 | Palestrant | 604/22 |
| 5,074,871 | 12/1991 | Groshong | 606/170 |
| 5,112,347 | 5/1992 | Taheri | 606/159 X |
| 5,152,773 | 10/1992 | Redha | 606/159 |
| 5,282,813 | 2/1994 | Redha | 606/159 |

FOREIGN PATENT DOCUMENTS

| 0649595 | 7/1993 | Australia | 606/159 |
|---|---|---|---|
| 1585065 | 1/1970 | France . | |
| 1935856 | 2/1971 | Germany . | |
| 2737014 | 3/1979 | Germany . | |
| 3320984 | 12/1984 | Germany | A61B 17/22 |
| 3800777 | 7/1988 | Germany | A61B 17/36 |
| 2044103 | 1/1987 | United Kingdom | A61B 17/22 |

*Primary Examiner*—Stephen C. Pellegrino
*Assistant Examiner*—Nancy Mulcare
*Attorney, Agent, or Firm*—Kane, Dalsimer, Sullivan, Kurucz, Levy, Eisele and Richard

[57] ABSTRACT

The instrument comprises an outer tube (1) fixed to the end of a flexible sheath (2), and an inner tube (3) displaceable in the outer tube and equipped with a head (5), to which is fixed a cylindrical casing (7) which has an inner boss (15). Arranged inside this casing are blades (10, 11) which are held axially on the outer tube by means of a collar (14) and which can swivel on the outer tube, this swiveling being ensured by the cylindrical casing (7), to be more precise by its end and by its inner boss (15) acting as a cam. This instrument, which is particularly robust, is intended for the removal of deposits formed on the inner walls of the arteries or veins.

4 Claims, 2 Drawing Sheets

MEDICAL INSTRUMENT FOR THE REMOVAL OF DEPOSITS FORMED ON THE INNER WALLS OF THE ARTERIES OR VEINS

BACKGROUND OF INVENTION

1. Field of the Invention

The present invention relates to a medical instrument for the removal of deposits formed on the inner walls of the arteries or veins, comprising an outer tube fixed to the end of a flexible tube or sheath intended to be introduced into the artery or the vein, an inner tube displaceable longitudinally in the outer tube, this inner tube being equipped, at its distal end, with a convex head exhibiting an axial passage continuing the inner tube, extensible cutting and scraping means, and means for ensuring the expansion and retraction of the cutting and scraping means under the effect of the relative longitudinal displacement of the two tubes.

2. Description of Prior Art

In the U.S. Pat. No. 5,074,871 an instrument of this type is described, in which the cutting and scraping means consist of flexible arms, the ends of which are articulated, on the one hand, on the integral convex head of the inner tube, and, on the other hand, on the end of the outer tube. When the convex head is brought near the end of the outer tube, the flexible arms deflect by buckling in such a way that an expansion of the cutting device is obtained. In the median part of some of the arms there is additionally cut out an aggressive tongue, which constitutes the actual cutting means. The retraction of the flexible arms is ensured by their inherent elasticity, as well as by the displacement in the opposite direction of the head. This head has an axial hole permitting the passage of a guide wire or of a catheter for inflating a balloon. Bearing in mind that, in accordance with the standards nowadays set down in surgery, the diameter of the introducer must not exceed 3 mm, so that the instrument has to have a diameter substantially less than 3 mm (in order to be able to staunch the blood), it is possible to appreciate the small dimensions of the hinge pins of the flexible blades and, consequently, the fragility of these hinges. Not only are the flexible blades and their attachments to the head and to the outer tube very fragile, but the problem of removing the material torn from the wall of the blood vessel has not been solved. It is proposed, in said document, to withdraw the material torn off by means of a catheter equipped with a balloon or a membrane surrounding the cutting head formed by the flexible arms. In both cases, the removal of the material torn off is by no means guaranteed, and, instead, there is a risk of a substantial quantity of material being entrained in the blood flow.

From the U.S. Pat. No. 4,794,928, an angioplasty instrument is also known, which comprises a catheter and expandable cutting means consisting of blades. These blades are either articulated on a support and controlled by cams, or consist of elastic arms which are spaced apart by the inflation of a balloon. No means is proposed for holding and removing the material torn off from the wall of the blood vessel.

The Patent DE 38 30 704 describes an instrument in which blades of a shell shape are mounted on a support made of elastically deformable material, the deformation of which, by means of a traction wire, provides for the expansion of the shells.

It has also been proposed to mount rigid blades at the end of a catheter and to control the spacing of these blades by means of a wire acting on connecting rods articulated at an intermediate point of the blades. Such a mechanism is not only fragile, given the small dimensions in which it has to be made, but it is in addition mechanically disadvantageous on account of the ratio of the forces present. In particular, when the blades, which are spaced apart, have scraped off a certain quantity of material, it is no longer possible in practice to close the blades. In addition, the problem of removing the material torn off from the wall of the blood vessel has not been solved. Furthermore, it is not possible in practice to have an inner tube for the injection of a liquid.

SUMMARY OF THE INVENTION

The object of the present invention is to provide an instrument obviating the disadvantages of the known instruments. More precisely, the object of the invention is to provide a very robust instrument which does not include a hinge, nor any other fragile component, and in which the retraction of the cutting and scraping means is guaranteed under all circumstances, and which makes possible to remove, that is to say withdraw from the blood vessels, all the material torn off from the wall of the blood vessel.

To this end, the medical instrument according to the invention is characterized by the fact that the convex head is equipped with a cylindrical casing surrounding the inner tube and of an external diameter equal to the diameter of the head, that the outer tube has, at its end opposite the convex head, a part having a diameter at least approximately equal to the external diameter of the cylindrical casing, and, at its opposite end, means for guiding the casing, that the cutting and scraping means are formed by at least two rigid blades in the shape of an elongated saddle extending longitudinally along and around the outer tube, inside said casing, and bearing via their convex face on the outer tube, the ends of the blades being at least approximately in contact with the wall of the casing in the retracted position, and that the means for ensuring the expansion of the blades are formed by an inner boss on the casing, having the function of a cam, the longitudinal displacement of which causes the blades to swivel on the outer tube, the retraction of the blades being effected by the end of the casing.

This design allows for a particularly robust construction which has no fragile hinge, functions reliably and includes only rigid components, the cross-section of which can guarantee their complete strength. This strength makes it possible in particular to ensure the retraction of the blades by the casing, even in the presence of an accumulation, between the blades, of material torn off from the wall of the blood vessel.

Furthermore, the material torn off can be held entirely inside the cylindrical casing, the latter being closed, in the retracted position, by the end of the outer tube.

The inner tube is used, in a conventional manner, for the passage of a wire guiding the catheter during its introduction into the artery or the vein to be treated. This inner tube can also be used for the injection of a treatment or contrast liquid. The number of blades can of course be greater than two, for example equal to three or four.

BRIEF DESCRIPTION OF THE DRAWINGS

The attached drawing represents, by way of example, one embodiment of the invention.

DESCRIPTION OF THE PREFERRED EMBODIMENT

Figure 1:
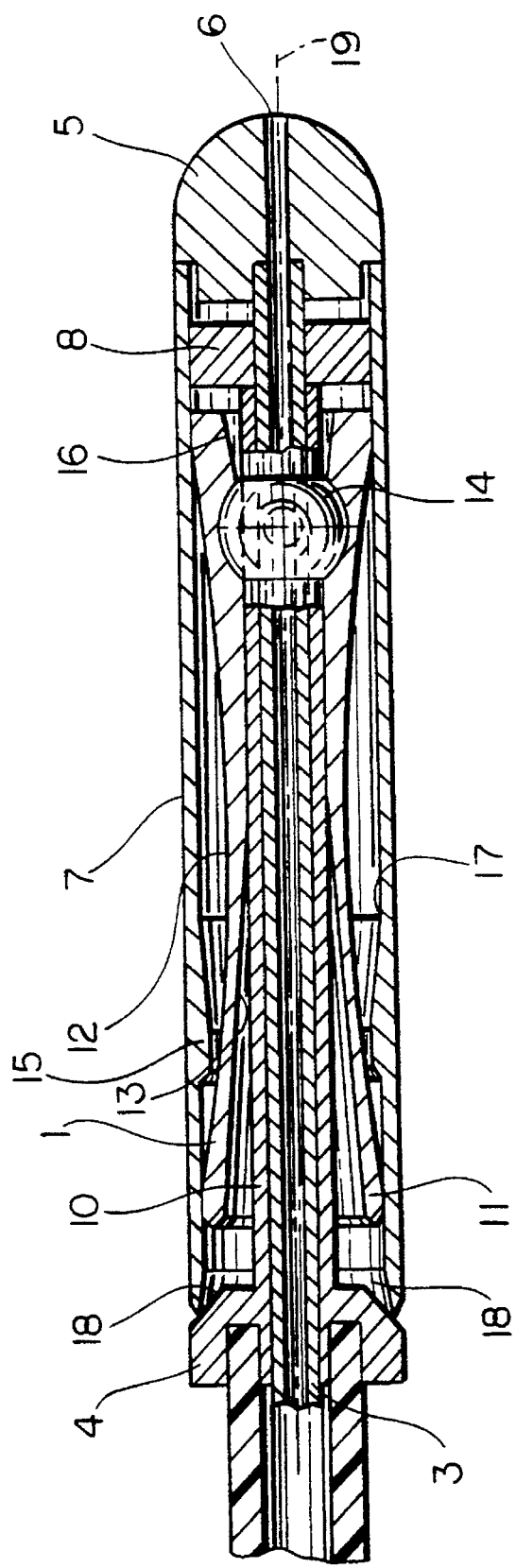
FIG. 1 is an axial cutaway view of the instrument, with the blades in a retracted position.

The instrument represented comprises a rigid outer tube 1, intended to be fixed to the end of a sheath 2 via its proximal end 4 of internal and external diameters greater than the corresponding diameters of the rest of the tube 1, and a flexible inner tube 3 of external diameter substantially equal to the internal diameter of the outer tube 1 and passing through the sheath 2 over its entire length, as well as the outer tube 1. The distal end of the inner tube 3 is equipped with a convex head 5, having more particularly a semispherical cap, through which an axial passage 6 forms a continuation of the inner tube 3. Fixed to this head 5 is a cylindrical casing 7, which surrounds the outer tube 1 and extends over almost the entire length of the latter. This casing 7 is guided axially by a cylindrical flange 8 formed at the distal end of the outer tube 1, the diameter of which flange is substantially equal to the internal diameter of the casing 7, the external diameter of which is equal to the diameter of the head 5 and to the diameter of the proximal part 4 of the outer tube 1. The casing 7 has an external diameter of 2.7 mm.

Inside the casing 7, between this casing and the outer tube 1, there are mounted, symmetrically with respect to the axis 19 of the instrument, two blades 10 and 11 in the shape of an elongated saddle, that is to say bodies whose faces are defined, at least approximately, by two coaxial hyperboloids of revolution. Each of the blades thus has, in the direction of the axis, a concave outer face 12 and a convex inner face 13. The blades 10 and 11 bear against the outer tube 1 via their convex face 13. Fixed on the outer tube 1, in proximity to the end 8, is a rounded collar 14 of semi-toric shape, holding the blades 10 and 11 axially, and on which the blades 10 and 11 can pivot, the blades having, for this purpose, a groove which is of a shape adapted to that of the collar.

The casing 7 additionally has, on its inner face, an annular boss 15, the cam function of which will be explained hereinafter in the description of the functioning of the instrument.

Figure 2:
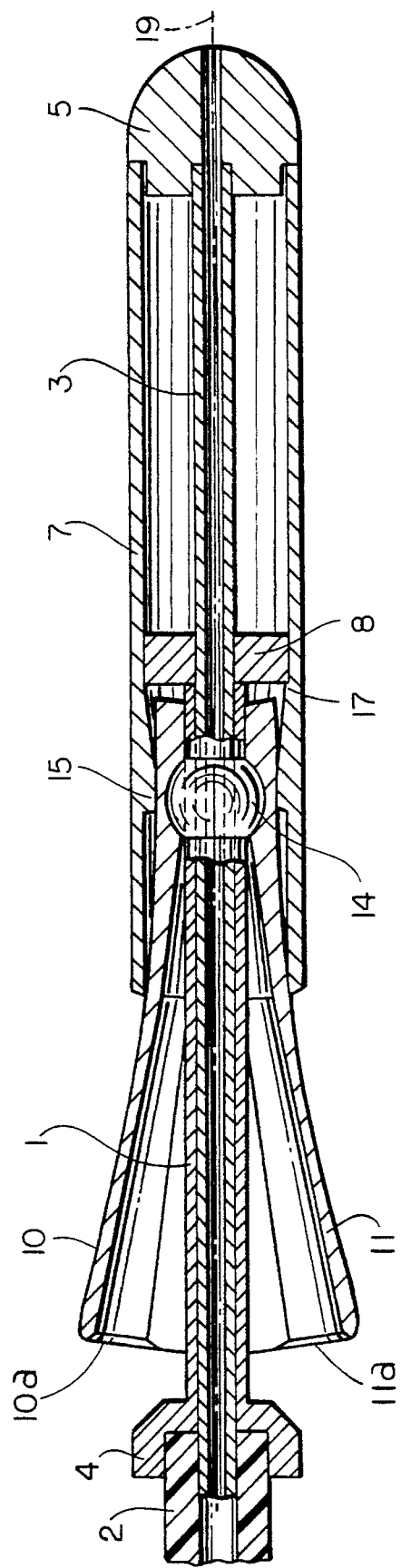
FIG. 2 is a similar view, with the blades in an expanded position.

Starting from the retracted or closed position represented in FIG. 1, if the operator wishes to space the blades 10 and 11 apart in order to perform a scraping of the inner wall of a blood vessel, he effects, by means of a suitable handle, the longitudinal relative displacement of the tubes 1 and 3, either by pulling on the outer tube 1, or by pushing the inner tube 3. These two actions can be combined. The operating handle can be, for example, of the type described in the U.S. Pat. No. 5,074,871 or of another known type. Upon this displacement, the boss 15 comes into abutment on the blades 10 and 11, the result of which is to swivel the blades on the outer tube 1. This swiveling is limited, on the one hand, by the end part 16 of the inner face of the blades which comes into abutment against the outer tube 1 and, on the other hand, by a shoulder 17, formed at the end of the boss 15, against which the cylindrical flange 8 comes into abutment. The blades are thus maintained in the open position, represented in FIG. 2, by blocking between the boss 15 and the outer tube 1. The blades 10 and 11 have a cutting edge 10a and 11a, respectively, making it possible to attack the deposit on the wall of the blood vessel by pulling on the sheath 2. The material torn off accumulates between the blades and the outer tube 1.

Once the scraping operation is finished, a traction is exerted on the inner tube 3, the effect of which is to return the cylindrical casing 7 in the direction of the end 4 of the outer tube 1. Upon this displacement, the boss 15 releases the blades 10 and 11 in order to permit, simultaneously, the end of the casing 7 to act in turn as a cam on the blades 10 and 11, so as to cause them to swivel in the other direction, that is to say close them again. The casing 7 being a closed cylindrical envelope, the radial force which it can exert on the blades 10 and 11 is considerable, and the material accumulated between the blades 10 and 11 does not prevent the closure of these.

When the casing 7 arrives at the end of its travel, its end comes into abutment against a bevel 18 of the end 4 of the tube 1, which completely closes the enclosure formed by the cylindrical casing 7 and the outer tube 1. The material torn off from the vessel and accumulated in the casing 7 can thus be withdrawn in its entirety from the blood vessel. By virtue of the closure of the blades, the material accumulates essentially in an annular chamber 18 formed in front of the part 4 of the tube 1.

We claim:

1. Medical instrument for the removal of deposits formed on the inner walls of the arteries or veins, comprising an outer tube (1) fixed to the end of a flexible sheath (2) to be introduced into the artery or the vein, an inner tube (3) displaceable longitudinally in the outer tube, this inner tube being equipped, at its distal end, with a convex head (5) exhibiting an axial passage being in fluid communication with a lumen of the inner tube and thus providing for a continuous passageway therefrom, expandable cutting and scraping means (10, 11) and means for ensuring the expansion and retraction of the cutting and scraping means under the effect of the relative longitudinal displacement of the two tubes, characterized by the fact that the convex head (5) is equipped with a cylindrical casing (7), concentric about the outer tube and surrounding the inner tube (1) and of an external diameter equal to the diameter of the head (5), that the outer tube (1) has, at its proximal end opposite the convex head, a diameter at least approximately equal to the external diameter of the cylindrical casing (7), and that the outer tube is provided at its distal end with cylindrical guide means for guiding the cylindrical casing, that the cutting and scraping means are formed by at least two rigid retractable blades (10, 11) having a retracted position and each having a convex face and being in the shape of an elongated saddle extending longitudinally along and around the outer tube, inside said casing, and bearing via their convex face on the outer tube, the shape is substantially that of two coaxial hyperboloids of revolution, an enclosable space existing between the casing and the outer tube in the retracted position, the ends of the blades being at least approximately in contact with the wall of the casing in the retracted position, and that the means for ensuring the expansion of the blades are formed by an inner camming boss (15) on the casing, having the function of a cam, the longitudinal displacement of the boss causes the blades to swivel on the outer tube (1), the retraction of the blades being effected by the end of the casing (7).

2. Instrument according to claim 1, characterized by the fact that, in the retracted position of the blades, the end of the casing (7) comes into contact with the proximal end of the outer casing, in such a way as to close the space delimited by the casing.

3. Instrument according to claim 1, characterized by the fact that the outer tube (1) is equipped with a means (14) for axial retention of the blades.

4. Instrument according to claim 2, characterized by the fact that the outer tube (1) is equipped with a means (14) for axial retention of the blades.

* * * * *